(12) United States Patent
Justi et al.

(10) Patent No.: US 7,927,866 B2
(45) Date of Patent: Apr. 19, 2011

(54) PROCESS CHALLENGE DEVICE FOR ASSESSING THE EFFECTIVE PERFORMANCE OF A BIOCONTAMINATION DEACTIVATION PROCESS

(75) Inventors: Christopher J. Justi, Morgantown, PA (US); Susan G. Quick, Kirtland, OH (US); Michael M. Tsentr, Solon, OH (US)

(73) Assignee: American Sterilizer Company, Mentor, OH (US)

( * ) Notice: Subject to any disclaimer, the term of this patent is extended or adjusted under 35 U.S.C. 154(b) by 1034 days.

(21) Appl. No.: 11/737,231

(22) Filed: Apr. 19, 2007

(65) Prior Publication Data
US 2008/0261296 A1    Oct. 23, 2008

(51) Int. Cl.
*C12M 1/34* (2006.01)
(52) U.S. Cl. .................. 435/287.4; 422/414; 422/417
(58) Field of Classification Search .............. 435/287.4; 422/414, 417
See application file for complete search history.

(56) References Cited

U.S. PATENT DOCUMENTS

| | | | |
|---|---|---|---|
| 3,440,997 A | 4/1969 | Rogen et al. | 116/114.5 |
| 4,348,209 A | 9/1982 | Murtaugh et al. | 23/232 |
| 4,353,990 A | 10/1982 | Manske et al. | 435/287 |
| 4,594,223 A | 6/1986 | Dyke et al. | 422/56 |
| 4,673,657 A | 6/1987 | Christian | 436/501 |
| D292,229 S | 10/1987 | Knudson et al. | D24/21 |
| 4,839,291 A | 6/1989 | Welsh et al. | 435/296 |
| 4,914,034 A | 4/1990 | Welsh et al. | 435/296 |
| D315,600 S | 3/1991 | Niven | D24/8 |
| 5,167,923 A | 12/1992 | Van Iperen | 422/58 |
| 5,405,580 A | 4/1995 | Palmer | 422/28 |
| 5,435,971 A | 7/1995 | Dyckman | 422/61 |
| 5,552,320 A | 9/1996 | Smith | 435/287.4 |
| 5,605,836 A | 2/1997 | Chen et al. | 435/305.4 |
| 5,750,184 A | 5/1998 | Imburgia | 427/2.13 |
| 5,801,010 A | 9/1998 | Falkowski et al. | 435/31 |
| 5,872,004 A | 2/1999 | Bolsen | 435/287.4 |
| 6,897,059 B2 * | 5/2005 | Foltz et al. | 435/287.6 |
| 7,435,381 B2 * | 10/2008 | Pugia et al. | 422/58 |
| 2002/0051733 A1 | 5/2002 | Antonoplos et al. | 422/56 |
| 2003/0087441 A1 * | 5/2003 | Lemus et al. | 436/1 |

FOREIGN PATENT DOCUMENTS

| | | |
|---|---|---|
| DE | 10 2004 040733 | 3/2006 |
| EP | 0914833 | 5/1999 |
| EP | 1704873 | 9/2006 |
| EP | 1707943 | 10/2006 |

* cited by examiner

*Primary Examiner* — William H Beisner
(74) *Attorney, Agent, or Firm* — Kusner & Jaffe; Michael A. Centanni

(57) ABSTRACT

A process challenge device (PCD) for determining the effectiveness of a microbial deactivation process that uses a vaporous deactivating agent (e.g., vaporized hydrogen peroxide) as a deactivating agent. The PCD includes first and second layers that are joined together to form (1) a chamber dimensioned to receive a biological and/or chemical indicator, and (2) first and second conduits fluidly connecting the chamber with a region outside the PCD. Each conduit has one end in communication with the region outside the PCD and another end in communication with the chamber. A removable seal member seals the biological and/or chemical indicator inside the chamber.

21 Claims, 5 Drawing Sheets

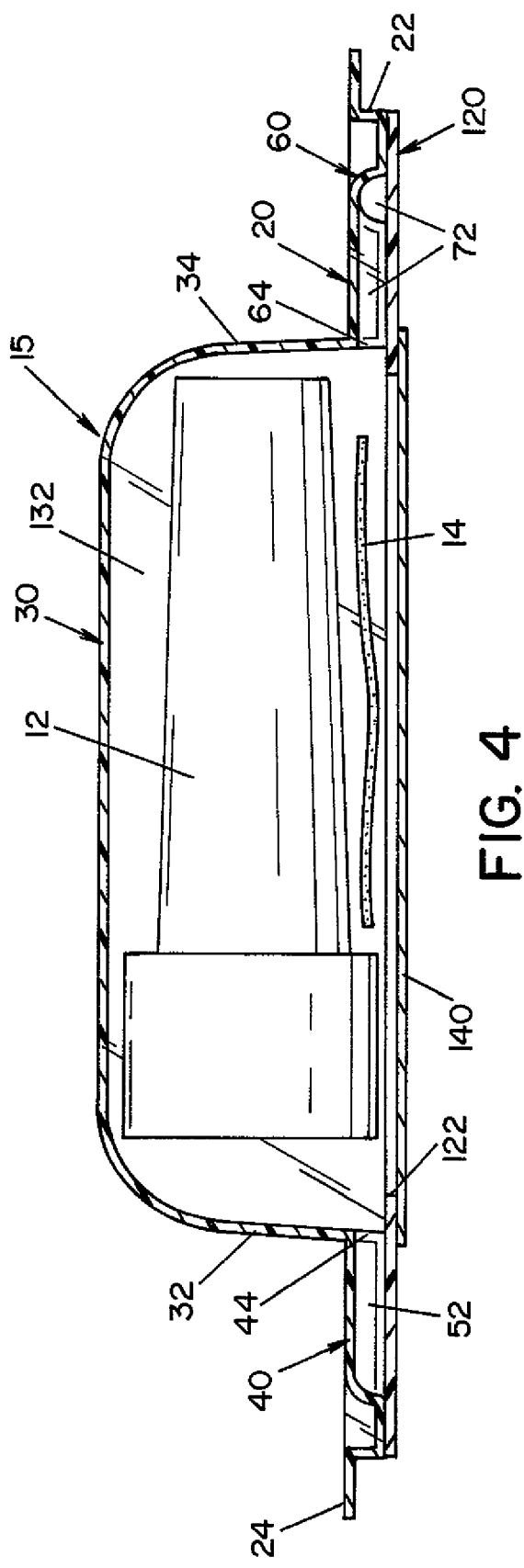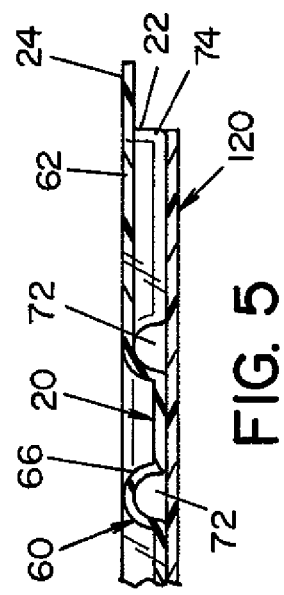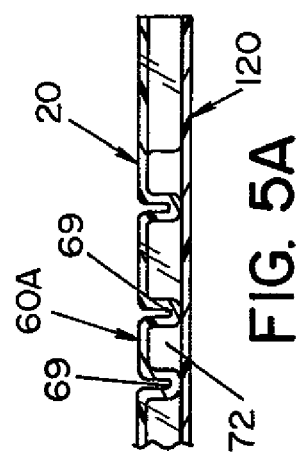

PROCESS CHALLENGE DEVICE FOR ASSESSING THE EFFECTIVE PERFORMANCE OF A BIOCONTAMINATION DEACTIVATION PROCESS

FIELD OF THE INVENTION

The present invention relates generally to monitoring of a biocontamination deactivation process, and more particularly to a process challenge device for assessing the effective performance of a biocontamination deactivation process.

BACKGROUND OF THE INVENTION

Medical instruments (such as dental, pharmaceutical, veterinary, and mortuary devices) that are exposed to blood or other bodily fluids require thorough cleaning and microbial deactivation between each use. Medical instruments may be microbially deactivated by exposure to a gaseous or vaporous deactivating agent, such as vaporized hydrogen peroxide, during a microbial deactivation process. For a medical instrument to be successfully deactivated during a microbial deactivation process, all surfaces of the medical instrument must be exposed to a predetermined minimum concentration of vaporized hydrogen peroxide for a predetermined minimum period of time.

Some surfaces of medical instruments are difficult to expose to the vaporous deactivating agent because of the shape, i.e., geometry, of the instrument. For example, for instruments having lumens, it is difficult to expose the inner surfaces of the lumens to the vaporous deactivating agent. As a result, a microbial deactivation process may not be effective because such surfaces have not been successfully deactivated by appropriate exposure to the vaporous deactivating agent.

A process challenge device (also commonly referred to as a "test pack") is designed to simulate an item being deactivated and to constitute a defined challenge to the microbial deactivation process. In order to assess the effectiveness of a microbial deactivation process a process challenge device (PCD) is placed within a deactivation chamber along with the instruments being deactivated. A PCD includes a housing and a biological indicator (BI) and/or a chemical indicator (CI), that are placed inside the housing. The housing includes internal passageways that create a challenge to the microbial deactivation process that is representative of the most difficult item to deactivate in a load. Following completion of a microbial deactivation process, the biological indicator and/or chemical indicator are analyzed in a known manner to determine the effectiveness of the microbial deactivation process.

A conventional PCD housing includes a narrow internal passageway formed therein that has an open end and a closed end. The open end of the passageway is in fluid communication with a region external to the housing. A BI and/or CI is disposed at the closed end of the passageway. During a microbial deactivation process, vaporized deactivating agent can travel from the region external to the housing, along the passageway, and to the BI and/or CI located at the closed end of the passageway.

One problem with existing PCD housings is that the passageway leading to the BI and/or CI can become partially or fully blocked, thereby causing the BI and/or CI to provide inaccurate results concerning the effectiveness of the microbial deactivation process. The passageway within the housing can become blocked as the result of several conditions. For example, condensation of the vaporous deactivating agent within the passageway can result in blockage of the passageway. The passageway can also become blocked when the walls defining the passageway collapse or are drawn into the passageway in response to pressure changes during the microbial deactivation process. For example, a known PCD housing includes a layer of flexible plastic film that defines a wall of the passageway. During a deactivation process, the flexible plastic film may collapse or be drawn into the passageway when the PCD is exposed to large changes in pressure, thereby reducing the diameter of the passageway. A PCD having a passageway with a reduced diameter provides a challenge greater than the most difficult item to deactivate in the load. Accordingly, the BI and/or CI may not provide accurate results.

Another problem with existing PCD housings is that the BI and/or CI of the PCD may not be exposed to the same concentration of vaporous deactivating agent (e.g., vaporized hydrogen peroxide) as the surfaces of the instruments being deactivated. It is believed that this inconsistency results from inadequate circulation of the vaporous deactivating agent within the PCD housing, as compared to the circulation of vaporous deactivating agent within the item (e.g., a lumened instrument) being deactivated.

The present invention overcomes these and other problems by providing a PCD that maintains a challenge to microbial deactivation that is representative of the most difficult item to deactivate in a load and can provide fluid circulation therein to provide appropriate exposure to a biological and/or chemical indicator.

SUMMARY OF THE INVENTION

In accordance with one embodiment of the present invention, there is provided a process challenge device for evaluating the effectiveness of a microbial deactivation process using a vaporous deactivating agent, the device comprising: a housing including: (a) a first layer, and (b) a second layer, wherein said first layer and said second layer are fixed to each other to define: (i) a chamber dimensioned to receive at least one of the following: a biological indicator and a chemical indicator, (ii) a first conduit having one end in fluid communication with said chamber and having an open end, and (iii) a second conduit having one end in fluid communication with said chamber and having an open end.

In accordance with another embodiment of the invention, there is provided a process challenge device for evaluating the effectiveness of a microbial deactivation process using a vaporous deactivating agent, the device comprising: (1) a housing including: (a) a first layer, and (b) a second layer fixed to the first layer, said first and second layers defining: (i) a chamber sealed by a removable seal member, (ii) a first tortuous conduit having one end in fluid communication with a first end of the chamber, and an open end, and (iii) a second tortuous conduit having one end in fluid communication with a second end of the chamber, and an open end; and (2) a least one of the following located in said chamber: a biological indicator and a chemical indicator.

An advantage of the present invention is the provision of a PCD for determining the effectiveness of a deactivation process that uses vaporized hydrogen peroxide to microbially deactivate medical instruments.

Another advantage of the present invention is the provision of a PCD housing that includes a passageway with two (2) open ends.

Still another advantage of the present invention is the provision of a PCD housing including a passageway defined therein by walls that are resistant to collapse in response to pressure changes.

Still another advantage of the present invention is the provision of a PCD housing having a passageway defined therein that is arranged to minimize condensation of a vaporous deactivating agent therein.

Still another advantage of the present invention is the provision of a PCD housing providing improved circulation of a vaporous deactivating agent therein.

Yet another advantage of the present invention is the provision of a PCD housing that allows convenient removal of biological and/or chemical indicators from the PCD housing.

Yet another advantage of the present invention is the provision of a PCD that can be manufactured simply and efficiently.

These and other advantages will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein:

FIG. 4 is a cross-sectional view of the PCD taken along lines 4-4 of FIG. 2;

FIG. 5 is a cross-sectional view of the PCD taken along lines 5-5 of FIG. 2;

FIG. 5A is a cross-sectional view taken along lines 5-5 of FIG. 2 illustrating an alternative embodiment of the PCD;

DETAILED DESCRIPTION OF THE INVENTION

Figure 1:
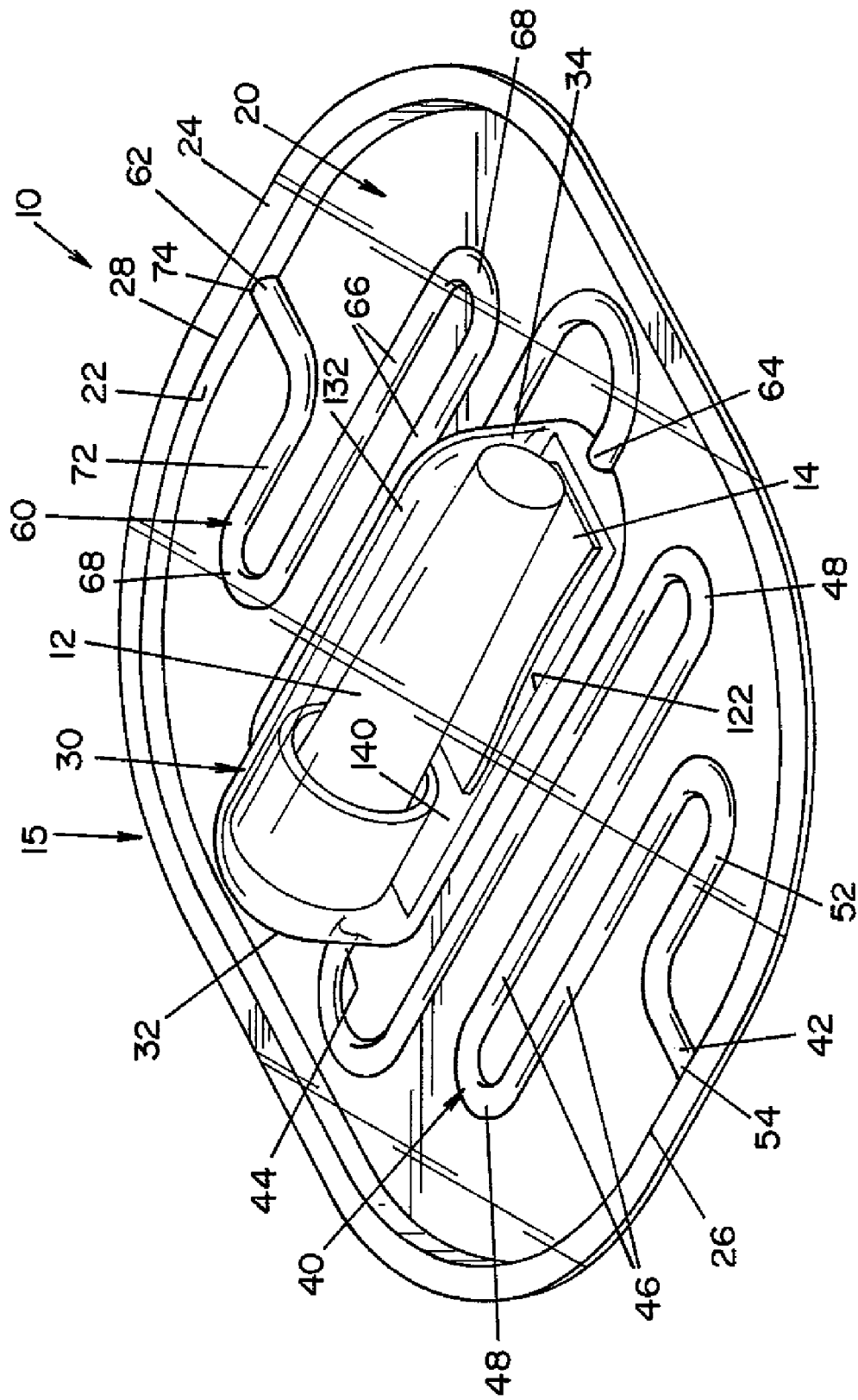
FIG. 1 is a perspective view of a PCD, illustrating one embodiment of the present invention.
Figure 2:
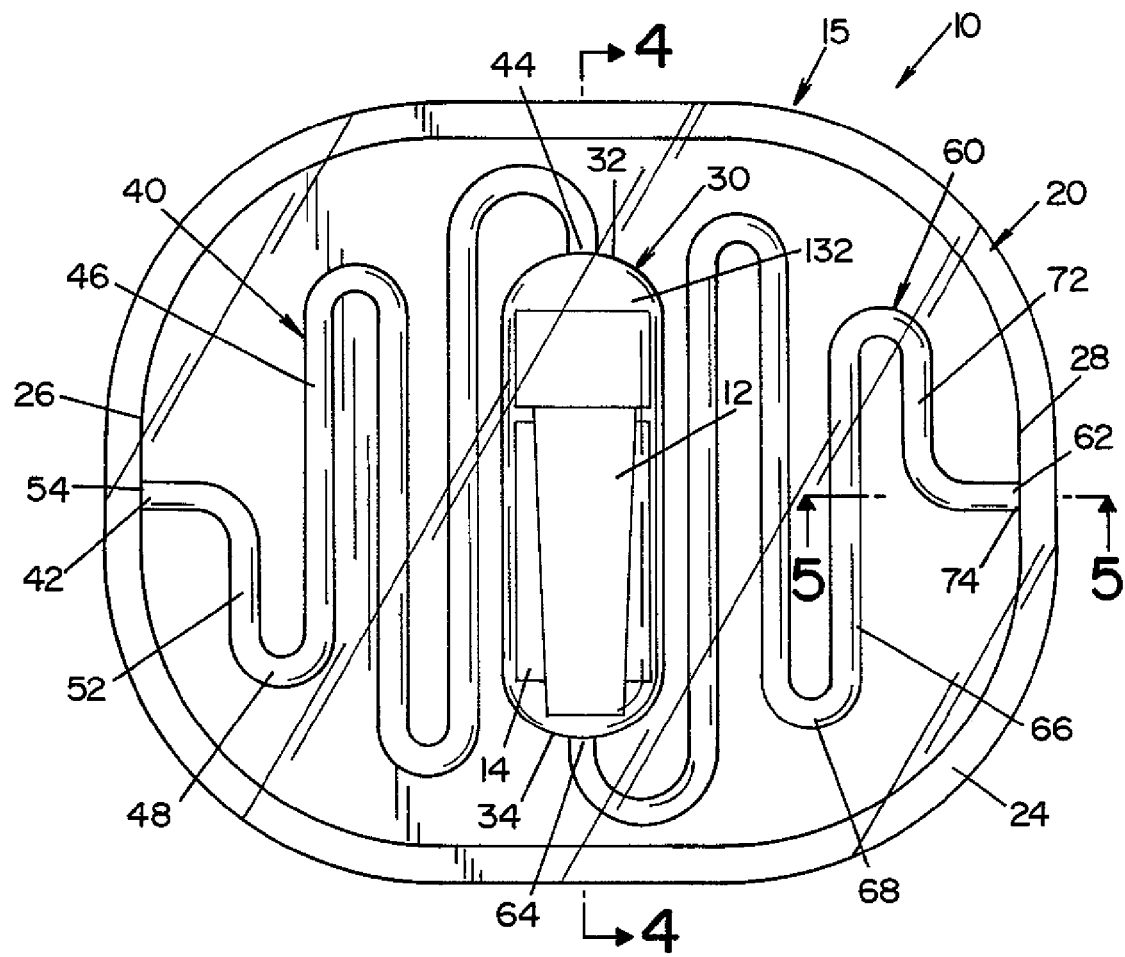
FIG. 2 is a top plan view of the PCD shown in FIG. 1.
Figure 3:
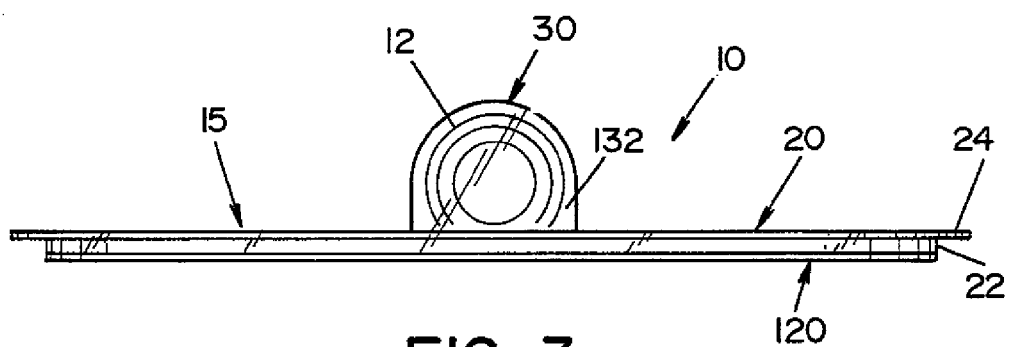
FIG. 3 is a side plan view of the PCD shown in FIG. 1.
Figure 6:
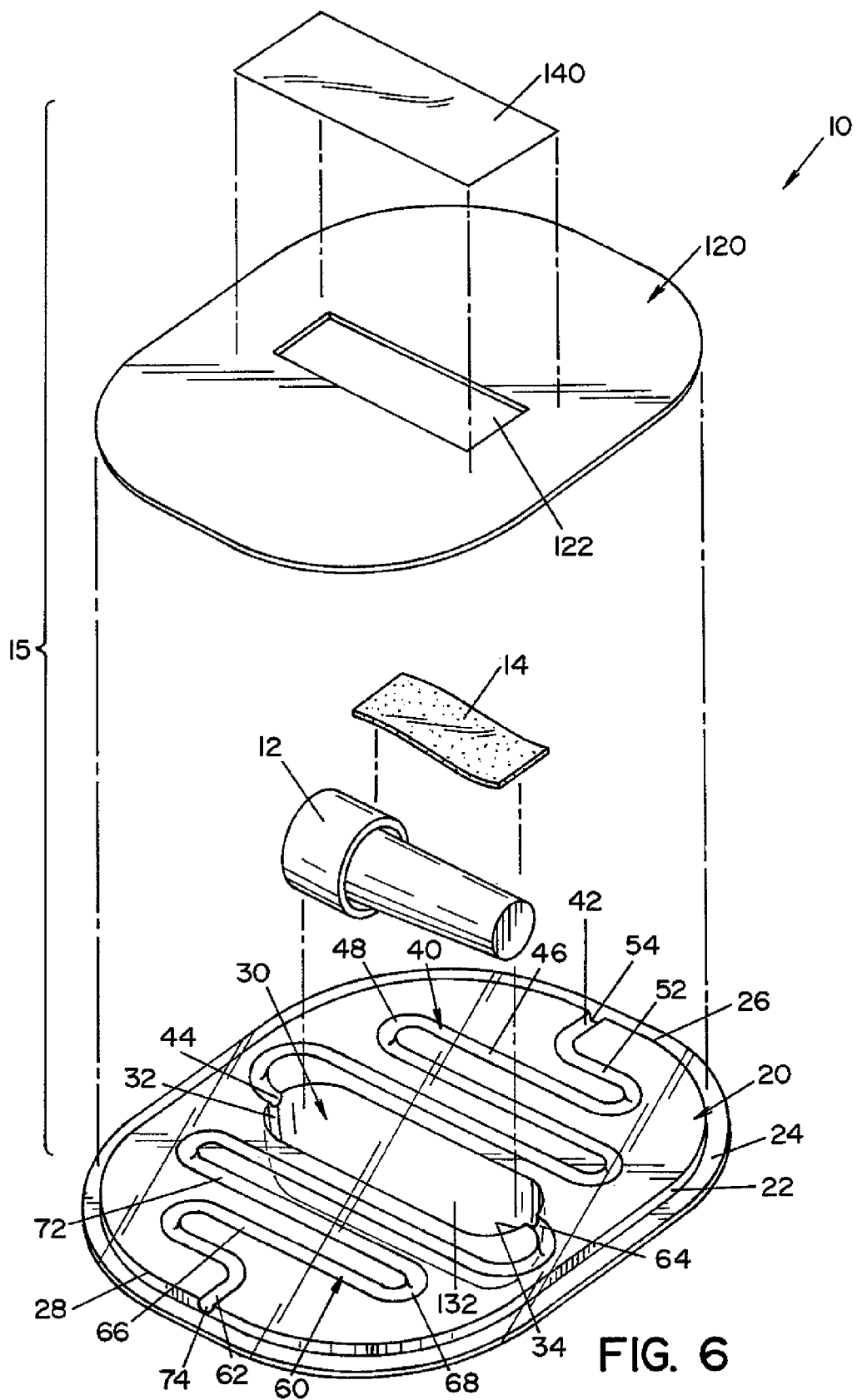
FIG. 6 is an exploded view of the PCD shown in FIG. 1.

Referring now to the drawings wherein the showings are for the purpose of illustrating one embodiment of the invention only and not for the purpose of limiting same, FIGS. 1-3 show a process challenge device (PCD) 10 according to one embodiment of the present invention. PCD 10 includes a housing 15 and an indicator device, such as a biological indicator (BI) 12 and/or a chemical indicator (CI) 14. Housing 15 is generally comprised of a first layer 20 and a second layer 120, as best seen in FIGS. 3 and 6.

First layer 20 is a generally planar sheet having a first end 26 and a second end 28. In the illustrated embodiment, a side wall 22 extends from the peripheral edge of first layer 20, and a flange 24 extends outward from side wall 22. Side wall 22 and flange 24 provide additional structural rigidity to first layer 20.

A recess 30, a first channel 40 and a second channel 60 are formed in first layer 20. Recess 30 has a first end 32 and a second end 34. In the illustrated embodiment, recess 30 is generally located in the center region of first layer 20. Recess 30 is dimensioned to receive BI 12 and/or CI 14.

First channel 40 extends between first end 26 of first layer 20 and first end 32 of recess 30. Accordingly, first channel 40 has an outer end 42 located at first end 26 of first layer 20 and an inner end 44 located at first end 32 of recess 30. Similarly, second channel 60 extends between second end 28 of first layer 20 and second end 34 of recess 30. Accordingly, second channel 60 has an outer end 62 located at second end 28 of first layer 20 and an inner end 64 located at second end 34 of recess 30. In the illustrated embodiment, first channel 40 includes generally straight portions 46 and bent portions 48. Likewise, second channel 60 includes generally straight portions 66 and bent portions 68. It should be appreciated that first and second channels 40, 60 can be formed in tortuous shapes other than as shown in the figures.

As best seen in FIGS. 3 and 6, second layer 120 is a generally planar sheet having dimensions similar to first layer 20. An opening 122 is formed in second layer 120. A seal member 140 covers opening 122, as will be described in detail below. It is contemplated that seal member 140 may be made of various different materials, including, but not limited to, a metal foil, a thermoplastic having a metallic layer deposited thereon, or a combination thereof, as well as polypropylene sheeting.

Second layer 120 is fixed to the lower surface of first layer 20, such that opening 122 generally aligns with recess 30, as best seen in FIG. 6. It is contemplated that second layer 120 may be fixed to first layer 20 in a variety of different ways, including, but not limited to, ultrasonic welding, solvent welding, an adhesive, or a combination thereof.

Opening 122 of second layer 120 is dimensioned to allow BI 12 and CI 14 to pass therethrough for insertion and removal from recess 30. Seal member 140 covers opening 122 to seal BI 12 and/or CI 14 within recess 30. An adhesive is preferably used to attach seal member 140 to second layer 120. Seal member 140 may be punctured, torn or peeled away to allow removal of BI 12 and CI 14 from recess 30 following a microbial deactivation process.

First layer 20 and second layer 120 are preferably formed of a generally rigid, thermoplastic material, including, but not limited to, polypropylene, polyethylene, polystryrene, and polyvinyl chloride (PVC).

It is contemplated that first layer 20 and second layer 120 may be alternatively formed from a single sheet that is folded to join first layer 20 to second layer 120. In this alternative embodiment, first layer 20 and second layer 120 are joined along a common edge.

When first layer 20 is fixed to second layer 120, first channel 40 and second layer 120 define a first conduit 52, and second channel 60 and second layer 120 define a second conduit 72, as best seen in FIGS. 1 and 2. Recess 30 of first layer 20, second layer 120, and seal member 140 define a chamber 132 when first layer 20 is fixed to second layer 120. First conduit 52 has an open end 54 at one end thereof and is in fluid communication with chamber 132 at the other end thereof. Likewise, second conduit 72 has an open end 74 at one end thereof and is in fluid communication with chamber 132 at the other end thereof. In accordance with a preferred embodiment, first and second conduits 52, 72 each have an inner diameter (ID) in the range of 1 to 2 mm, and each have a total length L in the range of 25 to 50 cm. Inner diameter ID and length L are preferably selected to be similar to the dimensions of a lumen of an instrument being deactivated. In the illustrated embodiment the respective lengths L and diameters ID of first conduit 52 and second conduit 72 are substantially the same.

First conduit 52, second conduit 72 and chamber 132 collectively define a continuous serpentine or tortuous pathway extending between open ends 54 and 74 to allow fluid flow through PCD 10.

In accordance with an alternative embodiment of the present invention shown in FIG. 5A, second channel 60A is defined by a plurality of depressions 69 formed in first layer 20. Likewise, first channel (not shown) is defined by a plurality of depressions (not shown) formed in first layer 20. In the illustrated embodiment, first layer 20 is attached to second layer 120 at the plurality of depressions 69.

In accordance with yet another alternative embodiment of the present invention it is contemplated that portions of first and second channels 40, 60 may be defined by second layer 120. Furthermore, it should be appreciated that first and second channels 40, 60 may be defined by portions of both first layer 20 and second layer 120.

In the illustrated embodiment, BI 12 is a conventional self-contained indicator device that includes a source of viable microorganisms, i.e., a biological challenge, and a source of nutrients. The source of nutrients is contained within a vapor impermeable container. The source of microorganisms is not exposed to the source of nutrients, unless the vapor impermeable container is opened, i.e., broken. The source of viable microorganisms is exposed to vaporous deactivating agent entering recess 30.

In the illustrated embodiment, CI 14 is a conventional indicator device comprised of a generally planar sheet that is coated or impregnated with a reactive chemical substance. The reactive chemical substance is selected such that a visual indication (e.g., a color change) results from exposure to a vaporous deactivating agent, such as vaporized hydrogen peroxide.

Assembly of PCD 10 will now be described with reference to FIG. 6. First layer 20 and second layer 120 are aligned with each other such that recess 30 of first layer 20 is aligned with opening 122 of second layer 120. As indicated above, first layer 20 and second layer 120 are fixed to each other by such means as ultrasonic welding, solvent welding, an adhesive, or a combination thereof. BI 12 and/or CI 14 are inserted through opening 122 of second layer 120, and placed inside recess 30 of first layer 20. Seal member 140 is then placed over opening 122 and fixed to second layer 120, preferably by use of an adhesive.

The present invention will now be described with respect to the operation of PCD 10. Generally, a deactivation device (e.g., a sterilization system), is used to expose medical instruments and devices to a microbial deactivating agent for microbial deactivation. The present invention is described herein with reference to a deactivation device that uses vaporized hydrogen peroxide as the deactivating agent. However, it will be appreciated that the present invention may be used in connection with deactivation devices that use other types of deactivating agents.

An instrument is placed within a deactivation chamber of the deactivation device, along with PCD 10. Vaporized hydrogen peroxide is injected into the deactivation chamber during a deactivation process to expose the instrument to vaporized hydrogen peroxide, thereby effecting microbial deactivation. Vaporized hydrogen peroxide entering the deactivation chamber also enters first and second conduits 52, 72 of PCD 10 via open ends 54 and 74. Vaporized hydrogen peroxide entering first and second conduits 52, 72 flows along a portion of a tortuous pathway to chamber 132, thereby exposing BI 12 and CI 14 to the vaporized hydrogen peroxide. As a result, the source of viable microorganisms within BI 12 is exposed to the vaporized hydrogen peroxide.

During portions of a deactivation process a vacuum may be drawn within the deactivation chamber in order to evacuate the deactivation chamber. For example, the pressure within the deactivation chamber may be reduced to less than 1 Torr. The use of a rigid material for first and second layers 20 and 120 prevents a collapse that may result in a partial or complete blockage of first conduit 52, second conduit 72 or chamber 132.

Figure 7:
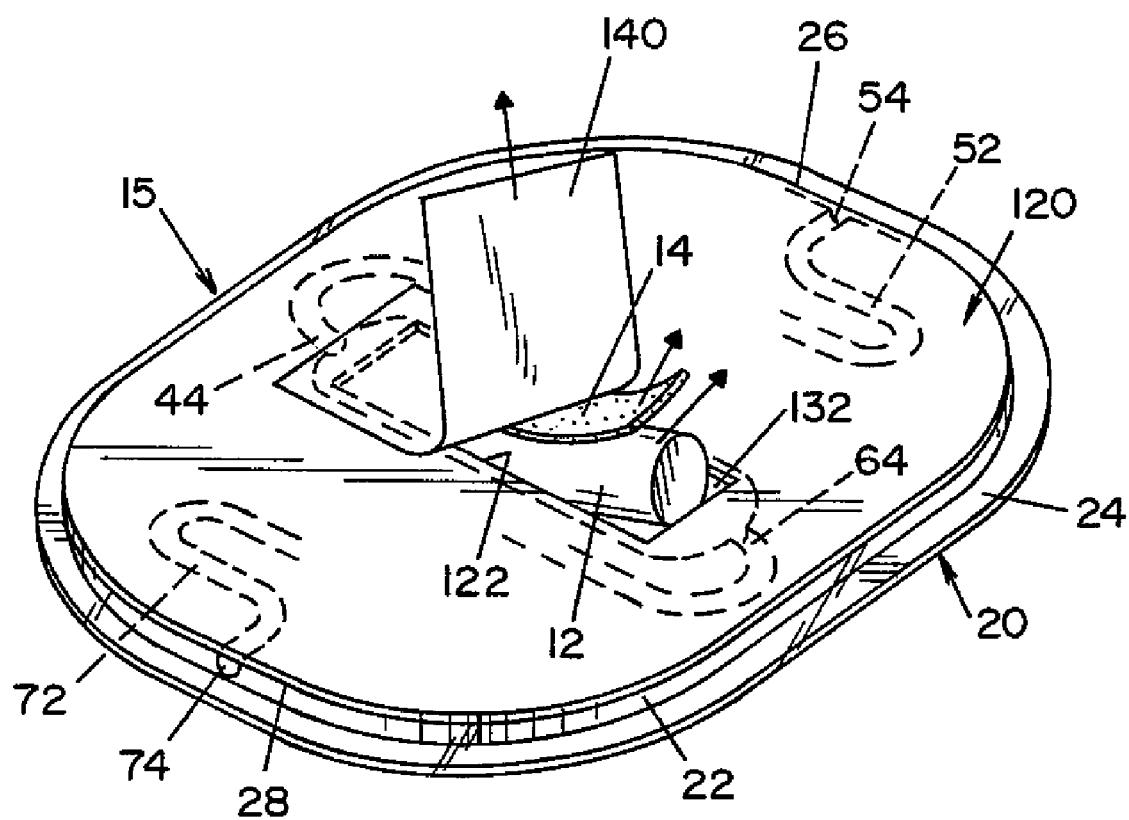
FIG. 7 is a perspective view of the PCD showing removal of indicators therefrom.

After the deactivation process has been completed, PCD 10 is removed from the deactivation chamber. Seal member 140 is either removed, punctured or peeled away to allow removal of BI 12 and CI 14 from recess 30, as shown in FIG. 7.

It should be appreciated that CI 14 may be visually inspected while located within recess 30 if first layer 20, second layer 120, and/or seal member 140, are made of a transparent material.

Following removal from recess 30, BI 12 may be activated by breaking the impermeable container or otherwise opening the impermeable container that contains the source of nutrients. In this manner, the microorganisms are exposed to the nutrients. BI 12 is then incubated for an incubation period of predetermined duration. If microorganisms within BI 12 are not deactivated by exposure to vaporized hydrogen peroxide during the deactivation process, the microorganisms will grow during an incubation period. Subsequent examination of BI 12 will determine whether any microorganism growth has occurred. Microorganism growth indicates that the deactivation process was ineffective and that the instruments exposed to the vaporized hydrogen peroxide along with PCD 10 were not effectively deactivated.

It should be appreciated that the dimensions of first conduit 52, second conduit 72 and chamber 132 are preferably selected such that PCD 10 simulates a "worst-case" instrument, i.e., an instrument having a geometry that is the most difficult to successfully deactivate by exposure to a vaporous microbial deactivating agent. Therefore, if PCD 10, as a worst-case instrument, is successfully deactivated during a deactivation process, then it follows that the instruments exposed to that same deactivation process were also successfully deactivated. Accordingly, if BI 12 shows no microorganism growth during the incubation period, then all microorganisms within BI 12 were deactivated during the deactivation process. Thus, it can be concluded that the instruments undergoing the same deactivation process have also been successfully deactivated.

The foregoing descriptions are specific embodiments of the present invention. It should be appreciated that these embodiments are described for purposes of illustration only, and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. A process challenge device for evaluating the effectiveness of a microbial deactivation process using a vaporous deactivating agent, the device comprising:
   a housing including:
      a first layer having an outer surface and an inner surface, wherein a first pair of depressions are formed in said outer surface to define double-walled side walls of a first channel formed in said inner surface of said first layer; and
      a second layer having an outer surface and an inner surface, wherein said inner surface of said first layer and said inner surface of said second layer are fixed to each other to enclose said first channel to form a first conduit having a first end and a second end,
      wherein said first layer and said second layer define a chamber dimensioned to receive at least one of the following: a biological indicator and a chemical indicator, said first end of said first conduit is in fluid communication with said chamber and said second end of said first conduit is open.

2. A process challenge device according to claim 1, wherein said second layer has an opening for accessing said chamber; and said process challenge device further comprises:
   a seal member for sealing the opening.

3. A process challenge device according to claim 2, wherein said seal member is comprised of at least one of the following: metal foil, polymeric film, and metalized polymeric films.

4. A process challenge device according to claim 1, further comprising:
   a second pair of depressions formed in said outer surface of one of said first and second layers to define double-walled side walls of a second channel in said inner surface of said layer, wherein the other of said first and second layers encloses said second channel to form a second conduit.

5. A process challenge device according to claim 4, wherein said first and second conduits respectively define tortuous pathways.

6. A process challenge device according to claim 1, wherein at least one of said first and second layers is transparent.

7. A process challenge device according to claim 1, wherein said first and second layers are comprised of a rigid thermoplastic material.

8. A process challenge device according to claim 1, wherein said process challenge device further comprises:
   a biological indicator.

9. A process challenge device according to claim 1, wherein said process challenge device further comprises:
   a chemical indicator.

10. A process challenge device according to claim 4, wherein said first and second conduits have substantially the same length L.

11. A process challenge device according to claim 10, wherein said length L is in the range of about 25 to about 50 cm.

12. A process challenge device according to claim 10, wherein said first conduit and said second conduit have substantially the same diameter D.

13. A process challenge device according to claim 12, wherein said diameter D is in the range of about 1 to about 2 mm.

14. A process challenge device for evaluating the effectiveness of a microbial deactivation process using a vaporous deactivating agent, the device comprising:
   (1) a housing including:
      (a) a first layer having a first side and a second side wherein a first pair of depressions are formed in said first side to define double-walled side walls of a first channel formed in said second side of said first layer, and
      (b) a second layer having a first side and a second side, wherein said first side of said second layer is fixed to said second side of said first layer at a location opposite said first pair of depressions to define a first tortuous conduit having a first end and a second end,
      wherein said first layer and said second layer define a chamber sealed by a removable seal member, said first end of said first conduit is in fluid communication with said chamber and said second end of said first conduit is open; and
   (2) at least one of the following located in said chamber:
      a biological indicator, and
      a chemical indicator.

15. A process challenge device according to claim 14, wherein said first and second layers are transparent.

16. A process challenge device according to claim 14, wherein said first and second layers are comprised of a rigid thermoplastic material.

17. A process challenge device according to claim 14, wherein said seal member is comprised of at least one of the following: metal foil, polymeric film, and metalized polymeric film.

18. A process challenge device according to claim 14, wherein said first tortuous conduit has a length of at least 12.5 cm.

19. A process challenge device according to claim 14, further comprising:
   a second pair of depressions formed in said first side of one of said first and second layers to define double-walled side walls of a second channel in said second side of said layer, wherein the other of said first and second layers encloses said second channel to form a second tortuous conduit, wherein said first and second tortuous conduits are in fluid communication with opposite ends of said chamber.

20. A process challenge device according to claim 19, wherein said second tortuous conduit has a length of at least 12.5 cm.

21. A process challenge device according to claim 19, wherein said first and second tortuous conduits have substantially the same length.

\* \* \* \* \*